(12) United States Patent
Cohen et al.

(10) Patent No.: US 7,942,839 B2
(45) Date of Patent: May 17, 2011

(54) APPARATUS FOR ISOLATING AN INJURED WRIST DURING AEROBIC EXERCISE

(76) Inventors: Stephen Roy Cohen, Cherry Hill, NJ (US); Leon I. Rosenberg, Cherry Hill, NJ (US)

(*) Notice: Subject to any disclaimer, the term of this patent is extended or adjusted under 35 U.S.C. 154(b) by 301 days.

(21) Appl. No.: 12/408,398

(22) Filed: Mar. 20, 2009

(65) Prior Publication Data
US 2010/0241042 A1    Sep. 23, 2010

(51) Int. Cl.
*A61F 5/00* (2006.01)

(52) U.S. Cl. .............. 602/16; 602/20; 602/21; 482/50; 482/93; 482/109

(58) Field of Classification Search .............. 602/16, 602/20–23, 26–27; 128/877–879; 482/44–50, 482/93–97, 106–109
See application file for complete search history.

(56) References Cited

U.S. PATENT DOCUMENTS

| | | | | |
|---|---|---|---|---|
| 2,214,052 A * | 9/1940 | Good | .............. | 482/105 |
| 2,617,650 A * | 11/1952 | Landis | .............. | 482/108 |
| 2,767,708 A * | 10/1956 | Keropian | .............. | 602/21 |
| 4,306,714 A | 12/1981 | Loomis et al. | | |
| 4,484,740 A * | 11/1984 | Green | .............. | 482/105 |
| 5,067,479 A | 11/1991 | Saringer et al. | | |
| 5,350,345 A * | 9/1994 | Frey | .............. | 482/105 |
| 5,403,002 A * | 4/1995 | Brunty | .............. | 473/438 |
| 5,788,607 A | 8/1998 | Baker | | |
| 6,013,044 A | 1/2000 | Estwanik | | |
| 6,142,914 A | 11/2000 | Crawford et al. | | |
| 7,048,674 B2 | 5/2006 | Hartman et al. | | |
| 7,303,507 B1 * | 12/2007 | Jozsa | .............. | 482/50 |
| 7,686,740 B1 * | 3/2010 | Chang | .............. | 482/50 |
| 7,837,641 B2 * | 11/2010 | Hoffman | .............. | 602/20 |

* cited by examiner

*Primary Examiner* — Michael A. Brown
(74) *Attorney, Agent, or Firm* — Michael B. Fein; Cozen O'Connor

(57) ABSTRACT

An exercise apparatus and method for isolating an wrist during aerobic exercise on an exercise machine such as a hand operated exercise bicycle or elliptical trainer, configured to be worn on the arm of a person having an wrist injury so that the person may operate the exercise machine with the arm having the wrist injury without pressure on the wrist, wherein weight and force are distributed from the exercise machine to the forearm and upper arm without implicating the wrist.

15 Claims, 6 Drawing Sheets

US 7,942,839 B2

APPARATUS FOR ISOLATING AN INJURED WRIST DURING AEROBIC EXERCISE

BACKGROUND OF THE INVENTION

The present invention relates an orthopedic device and method of use. More particularly, the invention relates to a system and method for isolating an injured wrist during aerobic exercise.

Many exercise devices of various types have been proposed and used, some of which being directed to specific body parts such as arms, arms, elbows, feet, fingers, or toes.

For example, U.S. Pat. No. 4,306,714 to Loomis, et al. discloses an exercise device for the hands or feet in which the user supplies the force and motion by one hand or foot which will be countered by a resistance and similar motion of the other hand or foot.

Crawford, et al., U.S. Pat. No. 6,142,914, discloses an exercise device for removable attachment to foot rests of a wheelchair to enable a person sitting in the seat of the wheelchair to exercise at least one of his or her arms and legs. The device includes a base slidably received on the foot rests and an exercising arrangement adjustably mounted on the base to accommodate the physical stature of a person sitting in the wheelchair.

Hartman, U.S. Pat. No. 7,048,674, disclosed a handheld device for exercising, rehabilitating and/or strengthening the muscles, tendons and ligament in the hands, wrists and/or forearm, as well as enabling the simultaneous improvement in the full range of motion in these regions which included an elongated adjustable locking member having a lower cushioned hand pad portion and an upper hand pad base, adjustably connected to an elongated finger grip bar. The finger grip bar included a finger grip receiving edge and a post attached to this edge for slidably receiving weights, enabling the wrists, hands and forearms to work together, enabling the user to exercise an injured or surgically repaired wrist, hand or forearm with the assistance of the uninjured wrist, hand or forearm, thereby reducing the overall duration of time needed for rehabilitation and recovery.

Baker, U.S. Pat. No. 5,788,607, disclosed a therapeutic wrist rotator for the passive rotation of the wrist of a user of the device for rehabilitation of the wrist after injury or disease. The device included a case which is adapted to be immovably affixed to a stationary object in order to resist the forces applied during use. The case includes an electric motor driving a reduction drive to provide relatively slow rotational speed and relatively high torque to an output shaft. The output shaft included a handgrip.

John Saringer, U.S. Pat. No. 5,067,479, disclosed a device for providing continuous passive motion therapy to a patient's wrist comprising a base removably attached to the forearm of the patient rearwards of the wrist. The base included horizontal turntable which can be secured thereon in a selected position. A wheel driven by a motor was rotatably mounted on the turntable for rotation in a vertical plane. A telescopic motion transmission which was provided between the wheel and a handle was mounted eccentrically to an eccentric disk which in turn was eccentrically and parallely mounted on the wheel. Rotation of the wheel and thus of the eccentric disk caused the motion transmission to pivot and to impart to the patient's hand a preselected pivoting motion about the wrist.

Joseph J. Estwanik, U.S. Pat. No. 6,013,044, disclosed a hand and wrist stabilization device for disposition on the hand and wrist of a user internally of a boxing glove to reduce relative movement of internal hand elements, specifically, the metacarpophalangeal joints, during impact resulting from boxing activities includes a flexible body, a metacarpophalangeal joint force dispersion pad attached to the body, an ulnar wrist stabilization strap, a radial wrist stabilization strap, and a contoured wrist compression strap attached to the body portion and a metacarpophalangeal joint stabilization member attached to the body all act to disperse force on the metacarpophalangeal joints while stabilizing the metacarpophalangeal joints against internal movement caused by impact force transmitted thereto during boxing activities.

However, no device has been disclosed or used for the specific purpose of isolating an injured wrist during aerobic exercise, or for facilitating exercise on an exercise machine by a person who has a wrist injury. Wrist injuries are usually treated by rigid casting, but even with rigid casts it is important not to put significant weight on the wrist or to apply significant force to the hand such as the force or stress on the wrist which occurs when using an exercise machine such as an elliptical trainer which has two shafts which must be pushed forward and pulled backward, or a hand operated exercise bike which has shafts which must be rotated with both hands. Because of the need to avoid force or pressure on the wrist having the wrist injury, exercise on exercise machines using the hand having the wrist injury was previously not possible or advisable. For individuals who wish to exercise when one of their wrists is injured, no prior device or apparatus was designed to facilitate such exercise.

It is an object of the present invention to facilitate exercise by individuals who suffer from a wrist injury. It is another object to facilitate aerobic exercise by such individuals while protecting an injured wrist from force, stress, and pressure. Another object is to facilitate such exercise on an exercise machine.

SUMMARY OF THE INVENTION

These objects, and others which will become apparent from the following description and drawings, are achieved by the present invention which comprises in one aspect an apparatus and method for isolating an wrist during exercise on an exercise machine designed to be worn on the arm of a person having the injury so that the person may operate the machine with the arm having the wrist injury without pressure on the wrist, wherein weight and force are distributed from an exercise machine engagement member to the forearm and upper arm without implicating the wrist.

In another aspect, the invention comprises an exercise apparatus for isolating an wrist during aerobic exercise on a exercise machine comprising a upper arm cuff, a forearm cuff, an outer elbow hinge joint, an inner elbow hinge joint, an inner upper bar joining the upper arm cuff to the inner elbow hinge joint, an outer upper bar joining the upper arm cuff to the outer elbow hinge joint, an exercise arm engagement member, an outer lower bar joining the exercise arm engagement member to the outer elbow hinge joint, an inner lower bar joining the exercise arm engagement member to the inner elbow hinge joint, and a forearm cuff engaging the inner lower bar or the outer lower bar or both the inner lower bar and the outer lower bar, the exercise arm engagement member configured to receive a shaft or bar of an exercise machine, the apparatus configured to be worn on the arm of a person having an wrist injury so that when the exercise arm engagement member receives the shaft or bar of the exercise machine, the person may operate the exercise machine by moving the shaft or bar with the arm having the wrist injury without pressure on the wrist, wherein weight and force are distributed from the shaft or bar to the forearm and upper arm without implicating the wrist.

Another aspect of the invention is a method of isolating a wrist while exercising on an exercise machine having a shaft or bar which is normally held by a hand of an individual comprising providing the aforementioned exercise apparatus, securing the upper arm cuff to the individual's upper arm, securing the forearm cuff to the individual's forearm while arranging the apparatus so that the elbow hinge joints are adjacent to each side of the individual's elbow, securing the exercise arm engagement member to a bar, arm, or crankshaft of an exercise machine, and operating the exercise machine in a normal manner, wherein the wrist of the individual is isolated from the force of the bar, arm, or crankshaft and such force is redistributed to the upper arm and the forearm.

In certain embodiments the inner forearm bar, outer forearm bar, inner upper arm bar, outer upper arm bar, and/or the elbow hinge joints are metal or plastic.

In some embodiments the upper arm cuff and/or forearm cuff includes Velcro material configured to maintain the cuff in a closed position around the upper arm or forearm of the person. Alternative embodiments include a clip to maintain the cuffs in a closed position. Such cuffs which include Velcro closures or clip closures are very well known. Some embodiments include two or three forearm cuffs. Some embodiments include two or three upper arm cuffs.

The engagement member, inner lower bar, and outer lower bar may be integrated as one single piece of metal or plastic, and can be a metal or plastic molding, for example. The engagement member may include a flat planar palm rest and the flat planar palm rest may include one or more horizontal shaft holders forming one or more horizontal holes, or may include a tubular horizontal shaft holder forming a single horizontal channel configured to receive an exercise machine shaft but not constrain the shaft from rotation when the apparatus is being used.

The flat planar palm rest can also, or alternatively, have a vertical shaft holder forming a vertical hole which is configured to receive a vertical shaft of an exercise machine such as an elliptical trainer, in which case the shaft will not usually rotate.

In operation, the individual having one or more injured wrists can use the apparatus to enable exercising on an elliptical trainer, exercise bicycle, or other type exercise machine having a shaft or bar, by securing the upper arm cuff to the upper arm, securing the forearm cuff to the forearm while arranging the apparatus so that the elbow hinge joints are adjacent to each side of the individual's elbow, placing a shaft through the hole or holes of the exercise machine engagement member, and operating the exercise machine in a normal manner. Use of the apparatus in this way isolates the injured wrist from the force of the bar or shaft and such force is redistributed to the upper arm and the forearm of the arm which has the wrist injury.

The apparatus can be worn around a cast, attached to a elbow brace, built into a cast, built into a elbow brace, or any other suitable configuration which does not interfere with the intended purpose of the apparatus and method.

The apparatus is especially useful for individuals who are accustomed to exercise for whom absence of ability to exercise when recovering from an wrist injury is a serious problem or inconvenience.

DETAILED DESCRIPTION

Figure 1:
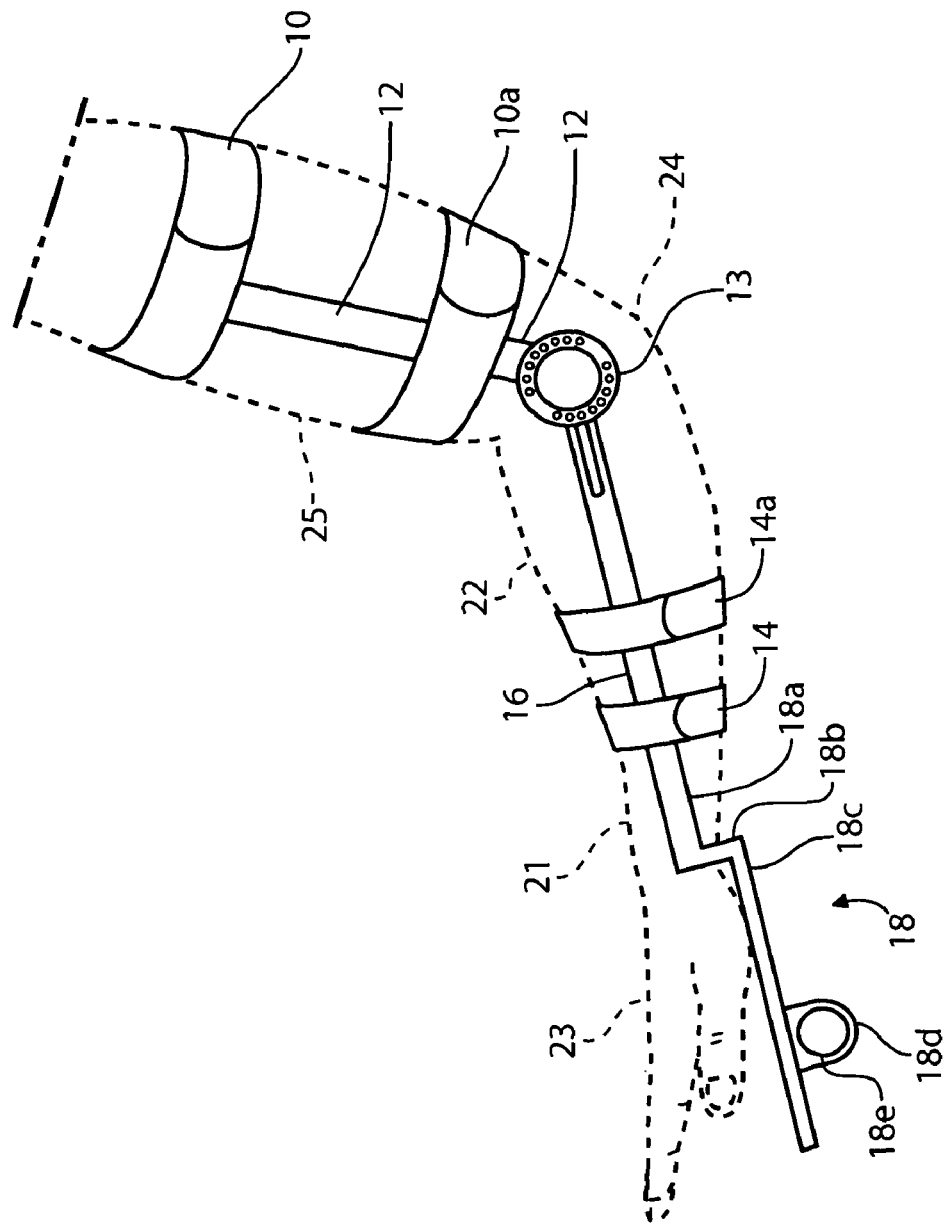
FIG. 1 is a side perspective view of an apparatus according to the invention being worn on an individual's arm.

In the drawings, reference numerals are consistent among the different views. Referring first to FIG. 1, an embodiment of an apparatus according to the invention is shown on an individual's arm having upper arm cuffs 10 and 10a secured to the individual's upper arm 25, an inner upper bar 12 connecting the upper arm cuffs 10, 10a, to an inner elbow hinge joint 13, which is adapted to allow the individual's arm to bend. The forearm 22 is secured to inner lower bar 16 by forearm cuffs 14, 14a, closed with Velcro material, and the wrist 21 is not engaged by the apparatus. The wrist 21 can be in a rigid cast, in which case the hand 23 would remain free, resting on flat palm rest 18c, which is a section of the engagement member 18.

The inner lower bar 16 in the illustrated embodiment is integrally connected to the palm rest 18c by forward portion of inner lower bar 18a and a vertical section 18b connecting the forward portion 18a with the palm rest 18c, all of which are a single molding of plastic or metal.

The palm rest 18c includes shaft holder 18d which forms a shaft receiving hole 18e and is configured to allow the shaft to rotate relatively freely in the hole.

Figure 2:
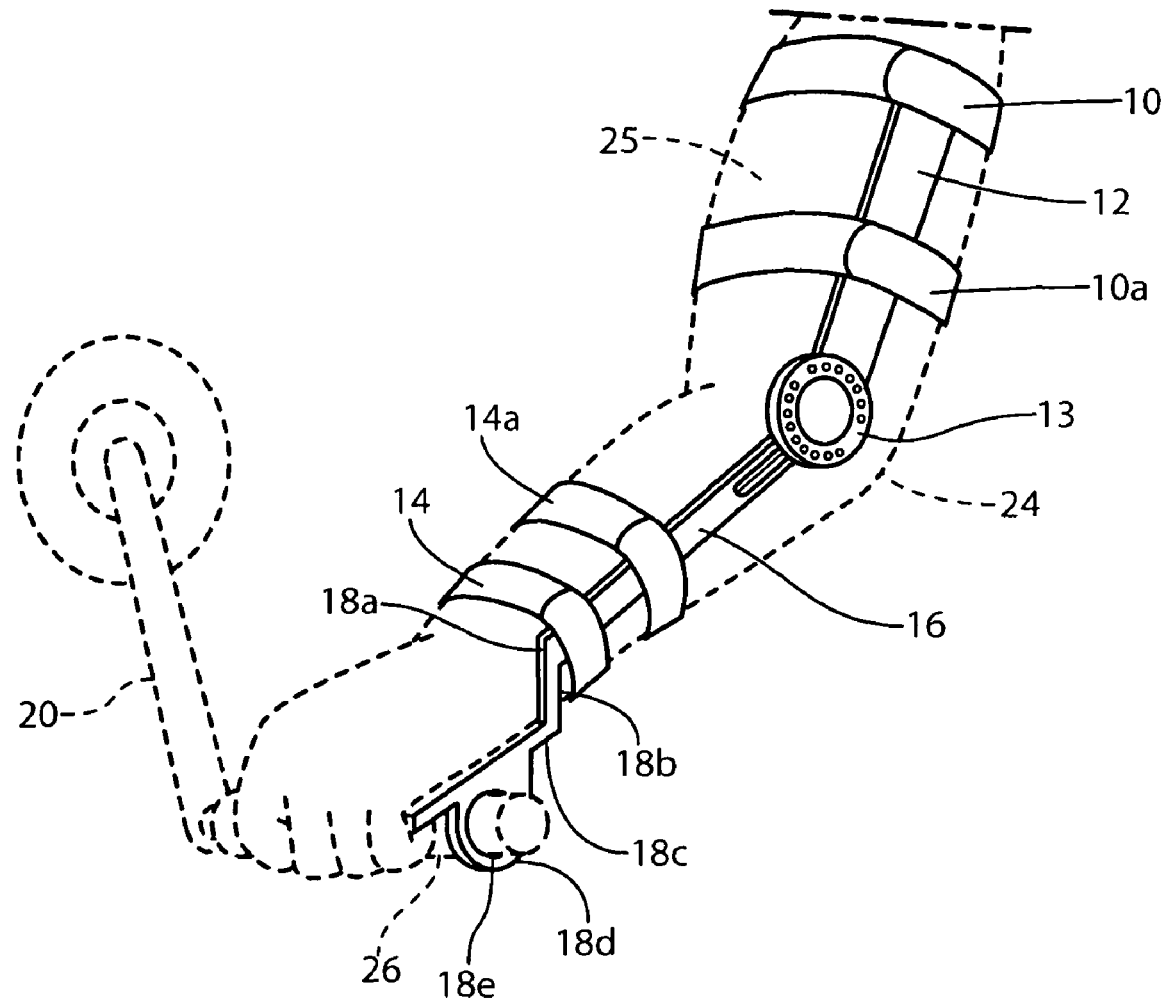
FIG. 2 is a side perspective view of an apparatus according to the invention illustrating a shaft of an exercise bicycle engaged through the holes of the engagement member.

Referring now to FIG. 2, the palm rest 18c is illustrated with a spindle 26 connected to crank 20, which are conventional parts of a hand operated exercise bicycle. The spindle 26 extends through shaft receiving hole 18k (FIG. 5) of shaft holder 18j (FIG. 5), and shaft receiving hole 18e in shaft holder 18d. The crank 20 can be rotated by the individual without implicating the wrist because the apparatus prevents the wrist from bending or receiving any stress. The force from the rotation is distributed to the forearm and upper arm by the apparatus of the invention.

Figure 3:
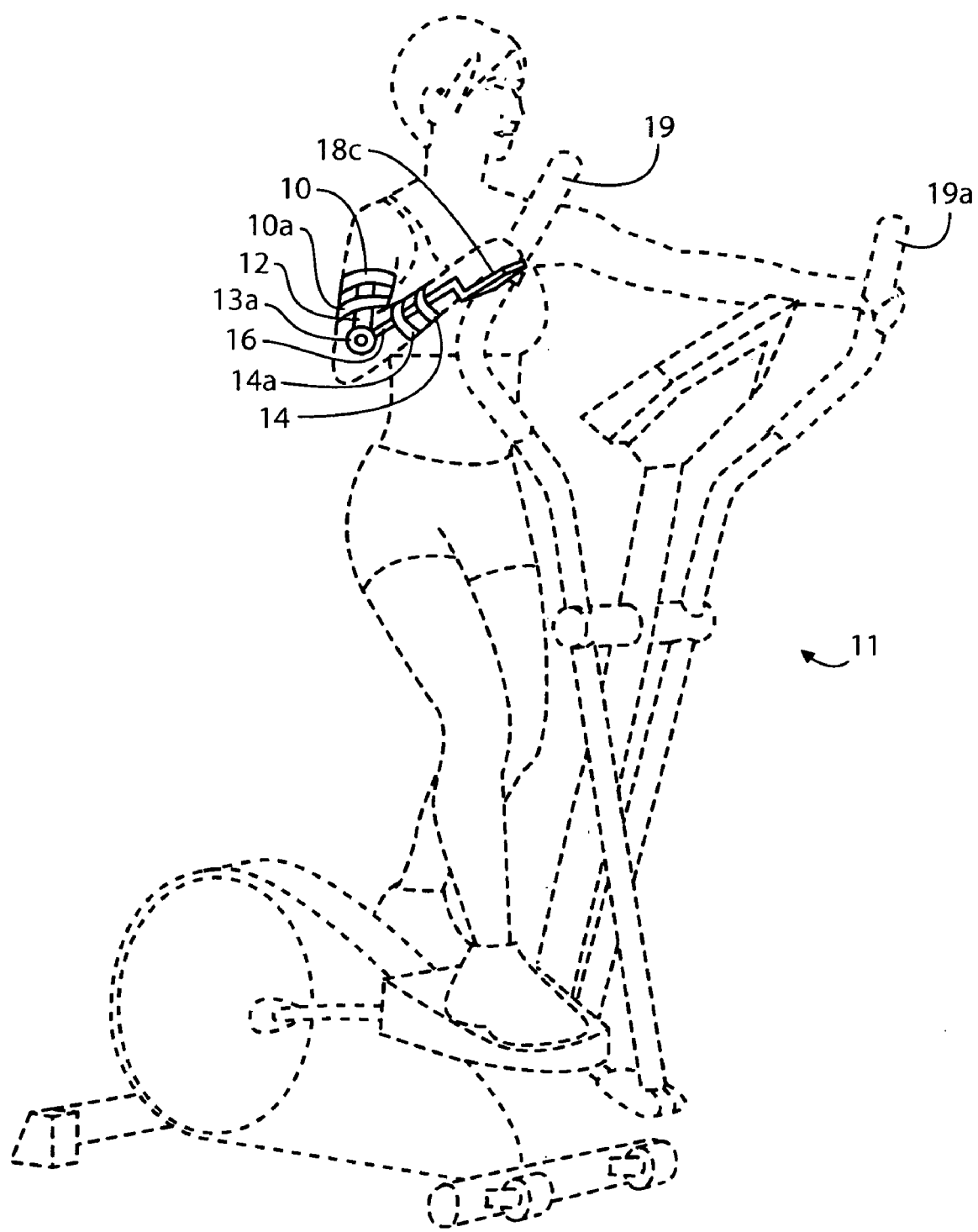
FIG. 3 is a side perspective view of an apparatus of the invention being worn by an individual using an elliptical trainer.

In FIG. 3, the individual with the injured wrist is illustrated wearing the apparatus of the invention, operating an elliptical trainer 11 having two vertical shafts 19, 19a.

Figure 4:
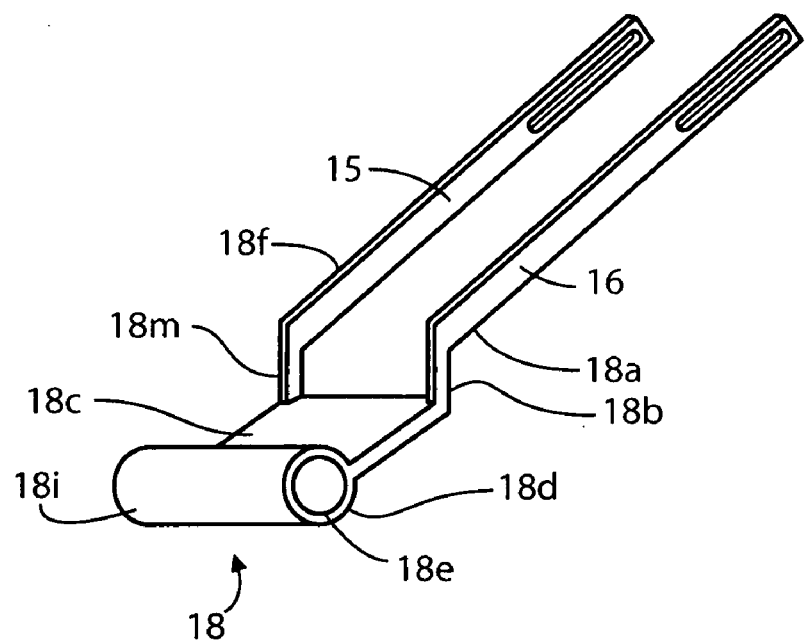
FIG. 4 is a side view of the bottom portion of an embodiment of an apparatus of the invention wherein the engagement member includes a tubular horizontal shaft holder.

FIG. 4 illustrates an embodiment of the integrated lower section of the apparatus wherein the inner lower bar 16 and outer lower bar 15 have forward sections 18a, 18f, connected through connecting sections 18b, 18m, to palm rest 18c having a tubular shaft holder 18i forming hole 18e.

Figure 5:
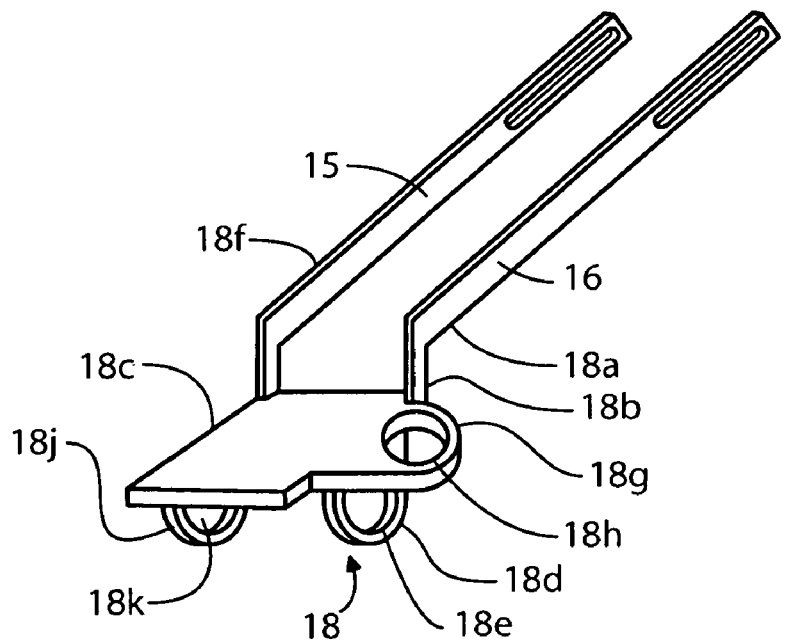
FIG. 5 is a side perspective view of the bottom portion of an embodiment of an apparatus of the invention wherein the engagement member includes two horizontal shaft holders and one vertical shaft holder.

FIG. 5 shows an alternative embodiment of a lower section having a section 18g of the palm rest 18c forming a vertical hole 18h for receiving a vertical shaft of an elliptical trainer exercise machine.

Figure 6:
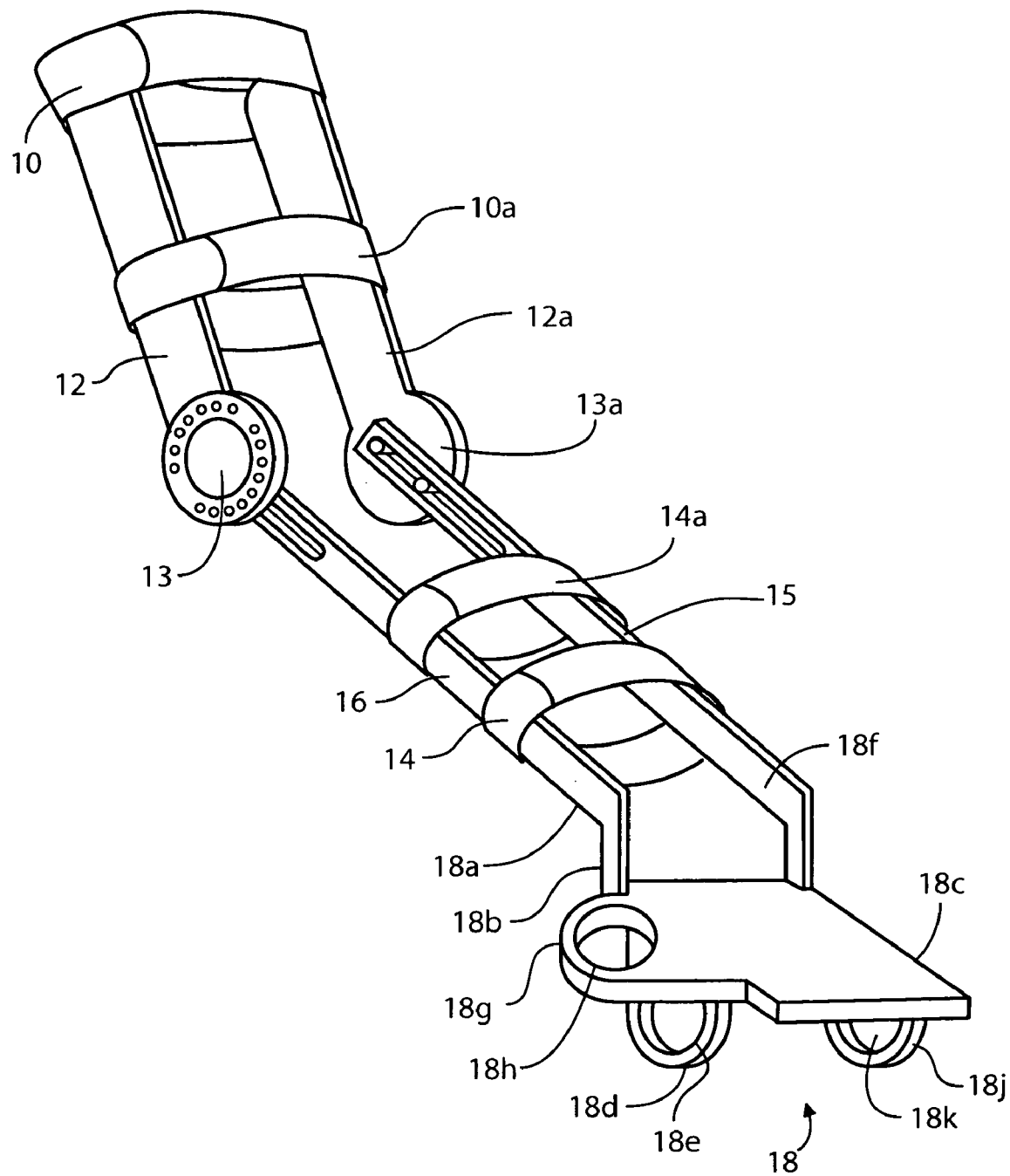
FIG. 6 is a side perspective view of an apparatus according to the invention illustrating two upper arm cuffs, two lower arm cuffs, a vertical hole in the palm rest for holding a vertical shaft, and two horizontal shaft holders for holding a horizontal shaft.

Referring now to FIG. 6, the lower section illustrated in FIG. 5 is shown connected to inner hinge 13 and outer hinge 13a.

Figure 7:
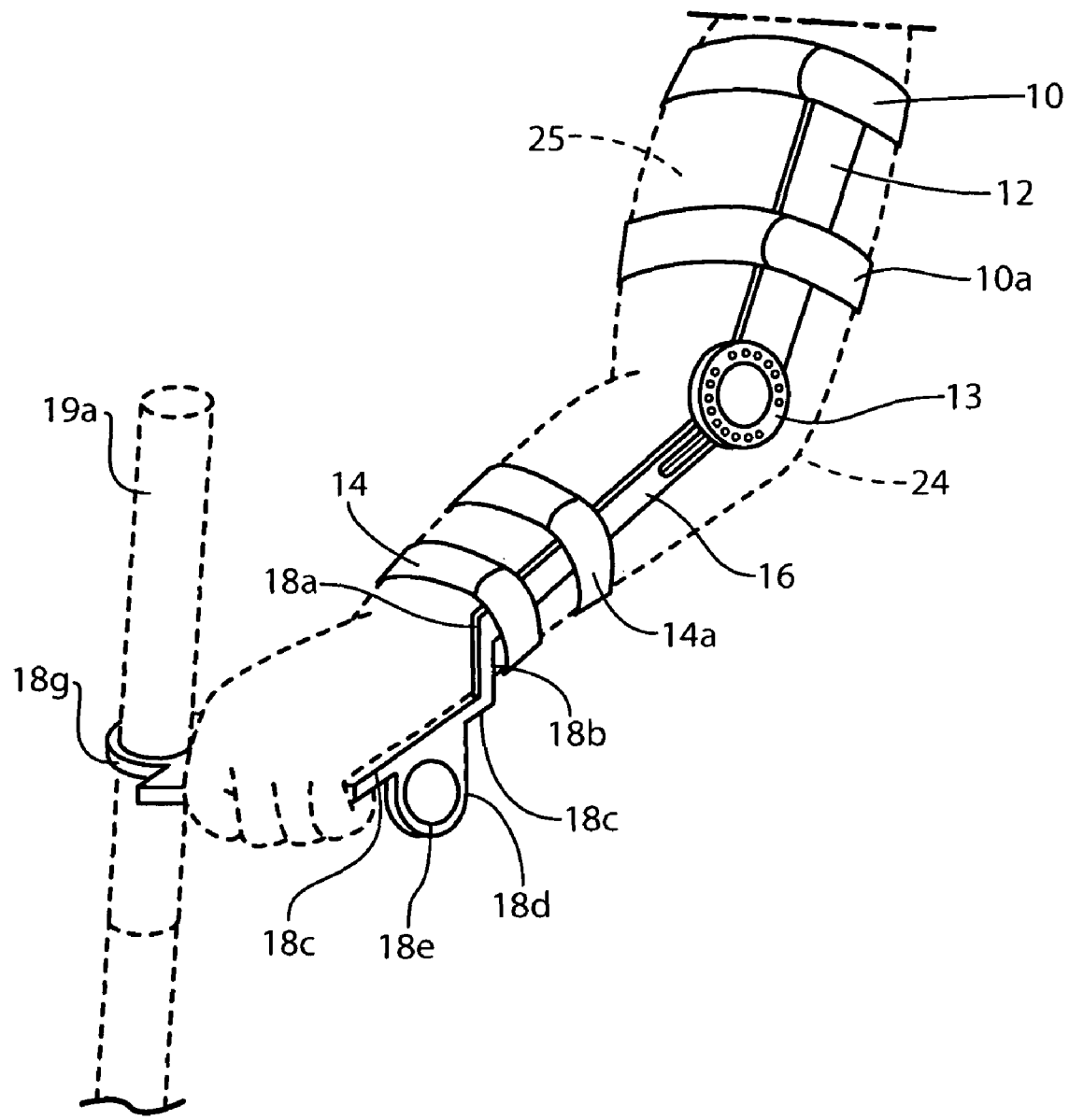
FIG. 7 is the embodiment of the apparatus of FIG. 6 illustrating the vertical hole holding a vertical shaft.

FIG. 7 illustrates the apparatus of the invention engaging vertical shaft 19 of an elliptical trainer machine through the vertical hole formed by vertical hole forming section 18g. In this embodiment, the horizontal hole 18e is not being used.

In general, the figures illustrate an apparatus for use by an individual with an wrist injury for cardiovascular exercise on an exercise machine by a method which comprises securing an upper arm cuff 10, or upper arm cuffs 10 and 11, to the individual's upper arm 25, securing a forearm cuff 14 or two forearm cuffs 14 and 14a to the individual's forearm 22 while arranging the apparatus so that the elbow hinge joints 13, 13a, are adjacent to each side of the individual's elbow 24, placing an exercise machine shaft through either the horizontal holes 18e or vertical hole 18h, and then using the machine in a normal manner while isolating the wrist of the arm on which the apparatus is engaged.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. An exercise apparatus for isolating an wrist during aerobic exercise on an exercise machine comprising an
   a. an upper arm cuff,
   b. an inner elbow hinge joint,
   c. an outer elbow hinge joint,
   d. an inner upper bar joining the upper arm cuff to the inner elbow hinge joint,
   e. an outer upper bar joining the upper arm cuff to the outer elbow hinge joint,
   f. an exercise arm engagement member,
   g. an outer lower bar joining the exercise arm engagement member to the outer elbow hinge joint,
   h. an inner lower bar joining the exercise arm engagement member to the inner elbow hinge joint, and
   i. a forearm cuff engaging the inner lower bar or the outer lower bar or both the inner lower bar and the outer lower bar,
   the exercise arm engagement member configured to receive a shaft or bar of an exercise machine, the apparatus configured to be worn on the arm of a person having an wrist injury so that when the exercise arm engagement member receives the shaft or bar of the exercise machine, the person may operate the exercise machine by moving the shaft or bar with the arm having the wrist injury without pressure on the wrist, wherein weight and force are distributed from the shaft or bar to the forearm and upper arm without implicating the wrist.

2. The apparatus of claim 1 wherein the inner forearm bar, outer forearm bar, inner upper arm bar, and outer upper arm bar are metal or plastic.

3. The apparatus of claim 1 wherein the inner elbow hinge joint and outer elbow hinge joint are metal or plastic.

4. The apparatus of claim 1 wherein the upper arm cuff or forearm cuff includes Velcro material configured to maintain the cuff in a closed position around the upper arm or forearm of the person.

5. The apparatus of claim 1 comprising two of three forearm cuffs.

6. The apparatus of claim 1 comprising two or three upper arm cuffs.

7. The apparatus of claim 1 wherein the exercise arm engagement member is configured to receive a spindle of an exercise bicycle and includes a hole arranged horizontally transverse to the lower arms and having a diameter slightly larger than a conventional spindle and is configured to allow the spindle to rotate freely within the hole when an individual wearing the apparatus is rotating the exercise bicycle.

8. The apparatus of claim 1 wherein the exercise arm engagement member includes a vertical hole having a diameter slightly larger than a conventional, generally vertical, reciprocating arm of an elliptical trainer, the hole configured to receive such a reciprocating arm and allow the individual to reciprocate the arm of the elliptical trainer.

9. The apparatus of claim 1 wherein the engagement member, inner lower bar, and outer lower bar are integrated.

10. The apparatus of claim 1 wherein the engagement member, inner lower bar, and outer lower bar are integrated and wherein the integrated engagement member, inner lower bar, and outer lower bar are a plastic molding.

11. The apparatus of claim 1 wherein the engagement member, inner lower bar, and outer lower bar are integrated and wherein the integrated engagement member, inner lower bar, and outer lower bar are metal.

12. The apparatus of claim 1 wherein the engagement member includes a flat planar palm rest.

13. The apparatus of claim 1 wherein the engagement member includes a flat planar palm rest having a horizontal shaft holder forming a horizontal hole.

14. The apparatus of claim 1 wherein the engagement member includes a flat planar palm rest having a vertical shaft holder forming a vertical hole.

15. A method of isolating a wrist while exercising on an exercise machine having a shaft or bar which is normally held by a hand of an individual comprising providing an apparatus according to claim 1, securing the upper arm cuff to the individual's upper arm, securing the forearm cuff to the individual's forearm while arranging the apparatus so that the elbow hinge joints are adjacent to each side of the individual's elbow, securing the exercise arm engagement member to a bar, arm, or crankshaft of an exercise machine, and operating the exercise machine in a normal manner, wherein the wrist of the individual is isolated from the force of the bar, arm, or crankshaft and such force is redistributed to the upper arm and the forearm.

* * * * *